(12) United States Patent
Aastrup et al.

(10) Patent No.: US 9,762,204 B2
(45) Date of Patent: Sep. 12, 2017

(54) PIEZOELECTRIC RESONATOR

(75) Inventors: Teodor Aastrup, Stockholm (SE); Jan Smith, Stockholm (SE); Henrik Anderson, Järfälla (SE)

(73) Assignee: ATTANA AB, Stockholm (SE)

( * ) Notice: Subject to any disclaimer, the term of this patent is extended or adjusted under 35 U.S.C. 154(b) by 830 days.

(21) Appl. No.: 13/329,894

(22) Filed: Dec. 19, 2011

(65) Prior Publication Data

US 2012/0090389 A1 Apr. 19, 2012

Related U.S. Application Data

(62) Division of application No. 10/542,616, filed as application No. PCT/SE2004/000175 on Feb. 11, 2004, now abandoned.

(30) Foreign Application Priority Data

Feb. 12, 2003 (SE) .................................... 0300375

(51) Int. Cl.
*H03H 9/13* (2006.01)
*G01N 9/00* (2006.01)
(Continued)

(52) U.S. Cl.
CPC ............ *H03H 9/132* (2013.01); *G01N 9/002* (2013.01); *G01N 11/16* (2013.01); *G01N 29/022* (2013.01);
(Continued)

(58) Field of Classification Search
USPC .................... 73/61.79, 64.53; 310/323.21
See application file for complete search history.

(56) References Cited

U.S. PATENT DOCUMENTS 3,260,104 A * 7/1966 King, Jr. ...................... 73/24.06
3,329,004 A 7/1967 King, Jr.
(Continued)

FOREIGN PATENT DOCUMENTS

EP 0453820 B1 10/1991
EP 1075082 A2 2/2001
(Continued)

OTHER PUBLICATIONS

English Machine Translation of EP0453820 (A2)—Oct. 30, 1991 "Sensor for Detecting a Substance in a Liquid" to Koesslinger.*
(Continued)

*Primary Examiner* — John Fitzgerald
(74) *Attorney, Agent, or Firm* — Banner & Witcoff, Ltd.

(57) ABSTRACT

A piezoelectric resonator for use in a sensor arrangement for detecting or measuring an analyte in a medium, comprises a quartz crystal plate, having a first crystal surface and a second crystal surface. The first crystal surface is provided with a first electrode, which has a surface area of less than 15 mm$^2$ and the second crystal surface is provided with a second electrode. The first electrode may have a rectangular surface shape. A flow cell for use in an apparatus for detecting or measuring an analyte in a medium, comprises walls that form a sensing chamber together with the resonator, and inlet and outlet openings for leading a fluid through the sensing chamber. A part of the resonator constitutes one of the walls of the sensing chamber and is arranged such that the first electrode is situated inside the sensing chamber.

19 Claims, 7 Drawing Sheets

(51) Int. Cl.
| | |
|---|---|
| *G01N 11/16* | (2006.01) |
| *G01N 29/02* | (2006.01) |
| *G01N 29/036* | (2006.01) |
| *G01N 29/22* | (2006.01) |
| *H03H 9/19* | (2006.01) |

(52) U.S. Cl.
CPC ......... *G01N 29/036* (2013.01); *G01N 29/222* (2013.01); *H03H 9/19* (2013.01); *G01N 2291/0256* (2013.01); *G01N 2291/02818* (2013.01); *G01N 2291/0421* (2013.01); *G01N 2291/0422* (2013.01)

(56) References Cited

U.S. PATENT DOCUMENTS

| | | | |
|---|---|---|---|
| 3,561,253 | A | 2/1971 | Dorman |
| 3,694,677 | A | 9/1972 | Guttwein et al. |
| 3,744,296 | A | 7/1973 | Beltzer |
| 3,872,411 | A | 3/1975 | Watanabe et al. |
| 3,879,992 | A | 4/1975 | Bartera |
| 4,242,096 | A | 12/1980 | Oliveira et al. |
| 4,562,725 | A | 1/1986 | Oka et al. |
| 4,644,804 | A | 2/1987 | Ramm et al. |
| 4,656,707 | A | 4/1987 | Berte et al. |
| 4,741,200 | A | 5/1988 | Hammerle |
| 4,789,804 | A * | 12/1988 | Karube et al. ............ 310/311 |
| 4,870,313 | A | 9/1989 | Hirama et al. |
| 5,201,215 | A | 4/1993 | Granstaff et al. |
| 5,235,240 | A | 8/1993 | Morita et al. |
| 5,455,475 | A | 10/1995 | Josse et al. |
| 5,501,986 | A | 3/1996 | Ward et al. |
| 5,552,274 | A | 9/1996 | Oyama et al. |
| 5,705,399 | A | 1/1998 | Larue |
| 5,744,902 | A | 4/1998 | Vig |
| 5,852,229 | A | 12/1998 | Josse et al. |
| 5,942,836 | A | 8/1999 | Yoshida et al. |
| 5,945,774 | A | 8/1999 | Shih et al. |
| 6,029,500 | A | 2/2000 | Tom |
| 6,106,149 | A | 8/2000 | Smith |
| 6,189,367 | B1 | 2/2001 | Smith et al. |
| 6,190,035 | B1 | 2/2001 | Smith |
| 6,196,059 | B1 | 3/2001 | Kosslinger et al. |
| 6,291,931 | B1 | 9/2001 | Lakin |
| 6,295,861 | B1 | 10/2001 | Tom et al. |
| 6,370,939 | B2 | 4/2002 | Smith et al. |
| 6,463,787 | B1 | 10/2002 | Schumacher et al. |
| 6,513,361 | B2 | 2/2003 | Miyake et al. |
| 6,525,449 | B1 | 2/2003 | Wajima |
| 6,755,073 | B2 | 6/2004 | Jakoby et al. |
| 7,045,931 | B2 * | 5/2006 | Yoshimine et al. ........ 310/322 |
| 7,055,377 | B2 * | 6/2006 | Paul et al. ............... 73/54.41 |
| 7,329,536 | B2 | 2/2008 | Zeng et al. |
| 7,501,744 | B2 * | 3/2009 | Yoshimine et al. ........ 310/340 |
| 2003/0076743 | A1 | 4/2003 | Thompson et al. |
| 2005/0039532 | A1 | 2/2005 | Ohsugi et al. |
| 2006/0053870 | A1 | 3/2006 | Berndt |
| 2009/0151428 | A1 | 6/2009 | Bhethanabotla et al. |

FOREIGN PATENT DOCUMENTS

| | | |
|---|---|---|
| GB | 2238907 A | 6/1991 |
| JP | 02118434 A | 5/1990 |
| JP | 04009742 A | 1/1992 |
| JP | 04236336 A | 8/1992 |
| JP | 06088779 A | 3/1994 |
| JP | 08075629 A | 3/1996 |
| JP | 2001013054 A | 1/2001 |
| JP | 2002246874 A | 8/2002 |
| WO | 0025118 A1 | 5/2000 |
| WO | 0212873 A2 | 2/2002 |
| WO | 0247246 A1 | 6/2002 |

OTHER PUBLICATIONS

Davis et al. "Continuous Liquid-Phase Pieozoelectric Biosensor for Kinetic Immunoassays," 1989, American Chemical Society, 61, 1227-1230.*

Thompson et al. "The Potential of the Bulk Acoustic Wave Device as a Liquid-Phaase Immunosensor," Mar. 1987, IEEE Transactions on Ultrasonics, Ferroelectrics and Frequency Control, Vo. UFFC-34, No. 2, pp. 127-135.*

Ward et al. "In Situ Intefacial Mass Detection with Piezoelectric Transducers," Aug. 31, 1990, Science, vol. 249, pp. 1000-1006.*

Josse et al.; (Jan. 15, 1998) "Analysis of the radial Dependence of Mass Sensitivity for Modified-Electrode Quartz Crystal Resonators"; Source: Analytical Chemistry, vol. 70, No. 2, pp. 237-247.

Lu et al.; (2004) "Quartz crystal microbalance with rigid mass partially attached on electrode surfaces"; Source: Sens Actuators, vol. 112, No. 3-4, pp. 203-210.

Lu et al.; (2005) "Finite element analysis of interference for the laterally coupled quartz crystal microbalances"; Source: Sensors and Actuators, vol. A, No. 119, pp. 90-99.

Rodahl et al.; (Jul. 1995) "Quartz crystal microbalance setup for frequency and Q-factor measurements in and liquid environments"; Source: Rev. Sci. Instrum., vol. 66, No. 7, pp. 3924-3930.

Rodahl et al.; (1996) "Frequency and dissipation-factor responses to localized liquid deposits on a QCM electrode"; Source: Sensors and Actuators B, 37, pp. 111-116.

Schweyer et al.; (1997) "A Novel Monolithic Piezoelectric Sensor"; Source: Proceedings of the 1997 IEEE International Frequency Control Symposium, Orlando, FL, pp. 32-40.

Sota et al.; Abstract Only—(2002) "A Versatile Planar Qcm-Based Sensor Design for Nonlabeling Biomolecule Detection"; Source: Anal. Chem., vol. 74, No. 15, pp. 3592-3598, DOI: 10.1021/ac025526b.

Voinova et al.; Abstract Only—(Oct. 2002) "Missing mass effect in biosensor's QCM applications"; Source: Biosensors and Bioelectronics, vol. 17, No. 10, pp. 835-841.

Wu et al.; (2003) "Robust design of quartz crystal microbalance using finite element and Taguchi method"; Source: Sens. Actuators, vol. B, No. 92, pp. 337-344.

* cited by examiner

PIEZOELECTRIC RESONATOR

CROSS REFERENCE TO RELATED APPLICATIONS

This application is a divisional application of U.S. patent application Ser. No. 10/542,616, filed Jul. 18, 2005, which is a U.S. National Stage Application under 35 U.S.C. §371 of International Application PCT/SE04/000175 (published as WO 2004/072622), filed Feb. 11, 2004, which claims the benefit of Swedish Patent Application SE 0300375-3, filed Feb. 12, 2003. Each of these applications is hereby incorporated by reference in its entirety.

TECHNICAL FIELD

The present invention pertains to a piezoelectric resonator, a flow cell comprising a piezoelectric resonator and sensor arrangement comprising a piezoelectric resonator.

BACKGROUND

A Quartz Crystal Microbalance (QCM) sensor arrangement utilizes the piezoelectric effect of a quartz crystal. In such a system a quartz crystal that is placed between two electrodes, which are connected to an AC-potential, begins to oscillate if the frequency of the AC-potential is close to the resonance frequency of the oscillation mode for the quartz crystal.

A typical QCM sensor arrangement comprises a thickness shear mode piezoelectric sensor unit, a sample insertion unit, a frequency counter, and signal presentation equipment and buffer and waste containers. A sample, which can contain any chemical substance of interest that can interact with the electrode of the sensor, is introduced into the sensor unit by the sample insertion unit. The sensor unit contains a piezoelectric resonator, a sensor chamber, flow channels to and from the chamber and an oscillating circuit. The sample induces an interaction with the piezoelectric sensor surface, which can in turn be observed by monitoring the oscillating characteristics of the crystal plate, e.g. by measuring changes in the piezoelectric resonator frequency, which resonator frequency typically is 5-50 MHz. The resonator utilized by the sensor unit includes a crystal plate, which is provided with electric contact areas for an electrode and a counter electrode on its surface, which electrodes are connectable to a signal source (e.g. an alternating voltage source) as well as to a measurement device. For measuring, one side of the piezoelectric crystal plate is brought into contact with the sample to be examined.

The crystal responds to the substance to be detected or to a change in the physical properties of the sample by an increase of associated mass on the electrode surface or a loss of associated mass on the electrode (i.e. a change in the mass that oscillates together with the crystal). Such a change in associated mass leads to an alteration of the resonance frequency and/or oscillation amplitude of the resonator.

Piezoelectric sensors can be used for analysis of the viscosity of a liquid sample and are particularly suitable for studying chemical and biochemical interactions.

The crystal plates utilised by piezoelectric resonators are usually oscillator quartz crystal plates. "A Novel Monolithic Piezoelectric Sensor", Schweyer et. al., 1997 IEEE International Frequency Control Symposium discloses a piezoelectric sensor which may be used for measuring purposes. In QCM sensor arrangements the resonator is typically arranged in a sensing chamber in which the sample is brought into contact with one of the electrodes (sensing electrode) of the resonator. Such a sensor arrangement is disclosed in EP 0 453 820 A2. The sensing chamber is often designed as a flow-through-cell, (see e.g. U.S. Pat. No. 6,196,059) such that the sample flow has its inlet at one end of the chamber and its outlet at another, whereby the sample can be lead though the chamber and meanwhile interact with the sensing electrode during its passage through the chamber. There is a continuously increasing demand of QCM sensor arrangements that have an improved sensitivity.

The object of the present invention is to provide a resonator and a flow cell for use in a sensor arrangement that has an improved sensitivity.

SUMMARY OF THE INVENTION

The object of the present invention is achieved by a thickness shear mode resonator as described in the claims.

The present invention thus relates to a thickness shear mode piezoelectric resonator for use in a sensor arrangement for detecting or measuring an analyte in a medium. The resonator comprises a quartz crystal plate having a first crystal surface and a second crystal surface, said first crystal surface being provided with a first electrode and said second crystal surface being provided with a second electrode characterised in that the first electrode has a surface area of less than 15 mm$^2$. This resonator has an improved sensitivity.

In one embodiment, the first electrode of the resonator has a surface area of less than 10 mm$^2$. In another embodiment the surface area of the first electrode is at least 0.05 mm$^2$, preferably 1-5 mm$^2$. The resonator of these embodiments has an even more improved sensitivity. The surface area of the first electrode is advantageously smaller than the first crystal surface, the first electrode preferably having a surface area that is 0.1-90% of the crystal area. The distance from the sensing electrode edge to the crystal edge is suitably at least 0.2 mm, preferably 1 mm and more preferably 2 mm.

In a preferred embodiment the first electrode surface has the shape of a rectangle, having a first side and a second side. This surface shape achieves a more immediate response to the substance to be detected. The rectangular shape of the electrode also renders it possible to achieve improved flow and sensor characteristics when used in a flow cell. The first side of the rectangle is preferably at least 0.1-10 times the second side.

Preferably, the first crystal surface of the resonator is provided with a first contacting area that is connected to the first electrode and the second crystal surface is provided with a second contacting area connected to the second electrode. The contacting areas facilitate the registration of the alterations in resonance frequency of the resonator. In the case a rectangular electrode is used, the first contacting area is preferably connected to the second side of the first electrode. Thereby the contacting area will not disturb the flow of fluid past the electrode.

In one embodiment the first and second surfaces of the quartz crystal are flat. A crystal with flat surfaces is easy to manufacture and therefore cheap to manufacture.

In another embodiment the quartz crystal is an inverted mesa, i.e. the crystal has at least a first recess on its first side in which the first electrode is provided. An inverted mesa has improved oscillating properties in comparison to other crystals and therefore improves the sensitivity of the QCM sensor arrangement. The first recess has a wall and a bottom surface. The area of the bottom surface is larger than the first electrode and the first electrode is arranged in the recess such that the part of the bottom surface that is not covered by the electrode surrounds the electrode on all sides. This distance between the electrode and the walls of the recess ensures that dampening of the crystal oscillation is avoided, whereby the sensitivity is improved. The shortest distance from the electrode edge to the recess walls is preferably at least 0.01 mm.

The present invention also relates to a flow cell for use in an apparatus for detecting or measuring an analyte in a medium, comprising walls forming a sensing chamber together with a resonator as described above, and inlet and outlet openings for leading a fluid through the sensing chamber, characterised in that a part of the resonator constitutes one of the walls of the sensing chamber and is arranged such that the first electrode is situated inside the sensing chamber. This flow cell enhances the flow characteristics of a fluid sample passing through the sensing chamber. The cross sectional area of the sensing chamber perpendicular to the flow direction is advantageously less than 2.5 times the cross sectional area of the inlet and outlet openings, and is most preferably the same as the cross sectional area of the inlet and outlet openings. The sensing chamber preferably has a volume of less than 2 µl.

In a preferred embodiment the flow cell comprises a flow cell element that includes an outwardly open recess, having a bottom surface and walls, whereby said bottom and walls constitute the walls of the sensing chamber not provided by the resonator, and wherein the resonator is a replaceable part, which is held against the flow cell element by a pressing force so as to cover the recess and thus form the flow cell. This is advantageous since the flow cell only comprises a few parts, which are easy to assemble, and the resonator is easily detachable, which facilitates the replacement of a used resonator with a fresh one. The flow cell element preferably comprises a contact surface, against which the resonator is to be held, which is plane-parallel to the bottom of the recess and which encircles the recess, and wherein the recess has a geometrical shape that corresponds to the geometry of the first electrode. The surface ensures the liquid tight contact between the flow cell element and the crystal surface and the geometrical shape of the recess further improves the flow characteristics in the sensing chamber. In another embodiment the flow cell comprises a flow cell element that includes an outwardly open recess, having a bottom surface and walls, whereby said bottom and walls constitute the walls of the sensing chamber not provided by the resonator, and wherein the resonator is attached to the flow cell element by an adhesive so as to cover the recess and thus form the flow cell. This flow cell is very easy to handle, since the whole flow cell is a pre-assembled replaceable part that does not require any skill in inserting into the QCM sensor arrangement. In both the above embodiments the shortest distance from the electrode edge to the recess walls preferably is at least 0.01 mm, whereby it is assured that the flow cell element does not disturb the oscillation of the resonator.

The present invention also relates to a sensor arrangement for detecting or measuring an analyte in a medium, characterised in that it comprises a flow cell as described above. This arrangement has an improved sensitivity.

DESCRIPTION OF THE EMBODIMENTS

Figure 1:
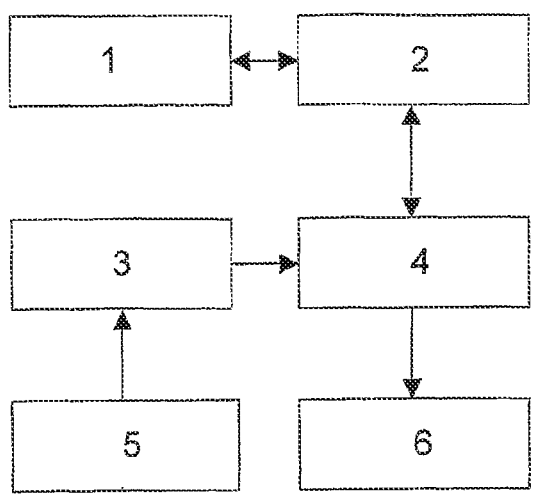
FIG. 1 shows a block diagram of a typical piezoelectric QCM sensor arrangement

The present invention is based on the surprising finding that a smaller sensing electrode area leads to a largely increased sensitivity of a piezoelectric resonator. The piezoelectric resonator of the present invention is intended for use in a sensor arrangement of a QCM system, such as the one schematically shown in FIG. 1, for sensing chemicals and/or chemical reactions in liquids or other fluid media. Such a QCM sensor system comprises a computer (PC) 1 for controlling and presenting data, a frequency counter 2, a sample insertion unit 3, a sensor arrangement 4, a buffer solution container 5 and a waste container 6. In use, a liquid or gaseous base flow is lead from the buffer solution container 5, through the sensor arrangement and across the resonator, which is arranged in a sensing chamber in the sensor arrangement 4 and is caused to oscillate at its resonance frequency, e.g. by an alternating voltage source. The sample, which may be liquid or gaseous, is injected into the sensor arrangement 4 and forced forward to the sensing chamber by means of the base flow. The sample thus enters the sensing chamber as a sample plug. As the sample passes the piezoelectric resonator the analyte in the sample interacts with the electrode provided on the resonator and thereby causes a change in the resonance frequency of the resonator. The frequency change is registered by means of the frequency counter 2. The sample is then lead to a waste container.

A typical resonator used in QCM sensor arrangements comprises a circular quartz crystal, which is provided with electrodes on both sides. The resonator has a sandwich structure with the quartz crystal in the middle. The thickness of the quartz crystal is given by the desired resonance frequency, or vice versa. On both sides of the crystal there might be an adhesive layer of for instance titanium, chromium, nickel, aluminium or alloys thereof. On top of the optional adhesive layer an electrode is arranged. The electrode is an electrically conductive material, the actual material chosen depends on the application but is normally gold, silver, titanium, chromium, nickel, aluminium, platinum, palladium or a metal alloy. The electrode materials may be different on each side of the crystal. The electrodes have traditionally been circular, with a diameter that is smaller than the diameter of the quartz crystal.

The substance to be detected normally binds to the electrode surface. In some applications the electrode that is to be exposed to the sample is provided with a specific surface coating, with which the substance to be detected then interacts. Such a surface coating has specific binding sites to which the substance to be detected binds. In some cases the substance to be detected may instead interact with the surface coating so as to remove material from the surface coating. In some applications the substance to be detected does not bind chemically to the electrode, but nevertheless interacts with the electrode (with or without coating), such that the oscillating properties of the resonator changes. Irrespective of how the substance to be detected interacts with the electrode, the detection or measuring operation results in a change in the associated mass of the electrode (i.e. a change in the mass that oscillates together with the crystal). Such a change in associated mass leads to an alteration of oscillating characteristics, e.g. the resonance frequency and/or oscillation amplitude of the resonator. Hereinafter the word "bind" shall be interpreted in this description so as to embrace also the interaction of the substance to be detected with the electrode, where the substance does not bind chemically to the electrode, but interacts with the electrode such that the oscillating properties of the resonator changes.

The crystal used in the resonator is normally AT-cut and has a circular or quadratic shape with a diameter of approximately 8-25 mm. An AT-cut crystal oscillates in a shearing motion. This is advantageous in liquid and gaseous applications, since it minimizes the energy loss to the surrounding media. Other crystal types such as thickness extension vibration mode or longitudinal mode crystals are less suitable for use in detecting/-measuring operations since the energy loss is too large. The electrodes on the AT-cut crystal are often of gold on both sides, but as mentioned above, other metals may also be used. The electrodes are very thin compared to the quartz crystal plate. Electrodes known in the art typically have an area of 20-400 mm$^2$.

As a consequence of the change of associated mass of the electrode during the detecting/measuring operation, the resonance frequency of the crystal plate will either decrease or increase and hence the change of resonance frequency can be measured to detect the change of associated mass of the electrode. In some applications (e.g. for analysis of gases in vacuum), the mass resolution of a QCM sensor arrangement can be as low as 1 pg/cm$^2$, corresponding to less than 1% of a monolayer of hydrogen.

The resonance frequency of the quartz crystal is a function of many parameters, apart from the change in associated mass, such as temperature, pressure, cut angel of the crystal, mechanical stress and thickness of the crystal. The resonance frequency is inversely proportional to the square root of the thickness of the crystal, and can be obtained by the Saurbrey equation: $\Delta f = -2f^2 \cdot \Delta m . \rho v \cdot A$, where f is the resonance frequency, $\rho$ the density of quartz, v the shear wave velocity in quartz, A the electrode area and $\Delta m$ the sample mass. Typical resonance frequencies used in liquid applications range from 1 MHz to 50 MHz.

It is technically difficult to make a small crystal plate oscillate in a liquid application. To be applicable for use in a sensor arrangement, the resonator must be able to withstand the stress exerted by clamping means by which the resonator is to be fixed in the sensing chamber of the sensor arrangement. It must also be able to withstand the load exerted by a liquid sample that is lead through the sensing chamber. The resonator must also have oscillating characteristics that enable oscillation also when clamped in the sensing chamber and the crystal plate must have a size and shape that allow clamping.

It has been found that one reason for insufficient sensitivity of the conventional resonators used for QCM sensor applications is related to the size of the sensing electrode, i.e. the electrode that is brought into contact with the sample. A high sensitivity is required for example within neuroscience and health diagnostics.

One parameter that affects the choice of electrode size to be chosen is the desired amount of active sites on the electrode surface. The number of active sites refers to the number of possible positions on the surface to which an analyte can bind. In the case of a study of protein adsorption on an uncoated metal surface the number of active sites is governed only by the area of the metal surface and the size of the protein. For a study of antigen-antibody interactions on a coated metal surface, the number of active sites is dependent on the number of antigens that can be immobilised on the surface. The number of active sites available on the sensor surface in turn determines the sensitivity range of the sensor arrangement.

The Q-value of the resonator is also an important parameter that has to be taken into account. A high Q-value has generally been regarded as a highly desired property in earlier disclosed resonators. The Q-value is a measure of the amount of energy stored in the system in relation to the amount of energy lost due to oscillation. This means that with a resonator with a high Q-value, little energy will have to be supplied to the crystal to ensure oscillation and the crystal is consequently easier to oscillate. Furthermore, a crystal with a high Q-value will provide a high signal to noise ratio when the frequency is measured. A high Q-value can be achieved by having a large electrode area, which is a reason why prior art resonators have been provided with relatively large electrode areas. When the electrode area becomes smaller the Q-value decreases until the crystal can not oscillate any more. The size of the electrode area must thus also be chosen with careful consideration of the Q-value.

The attachment of the crystal into the flow system also affects the load of the crystal, since the attachment may cause a damping on the crystal. The crystal load also depends on with what type (if any) media the electrode is coated with (e.g. antibodies, Molecular Imprinted Polymers) and which type of fluid the sample and the base flow are (air, aqueous, oil etc). An increased load on the crystal, which may be due to surface coating, clamping or fluid viscosity, lowers the Q-value of the crystal in operation and may require a larger electrode area to maintain the oscillation.

The size of alteration of the resonance frequency is dependent on the size of alteration of the associated mass. It has now been found that a smaller electrode area result in a higher sensitivity, since the alteration in resonance frequency is dependent on the alteration in the mass of the electrode, which is caused by the interaction between the electrode and the substances to be detected/measured. A certain change in associated mass in absolute measures constitutes a larger relative change to the total associated mass if the electrode area is smaller, whereby the relative change in the electrode weight will be a larger for a smaller electrode area. This will in turn lead to a larger change in the oscillation frequency. The area of the electrode must, however, be chosen with consideration to the amount of active sites needed, to the Q-value and to the load of the crystal. It has been found that the sensing electrode should have a surface area of between 0.05 and 15 mm², preferably 1-5 mm² in order to obtain a satisfying sensitivity in sensing applications for detection or measuring of analytes in liquid or gaseous media.

Figure 2:
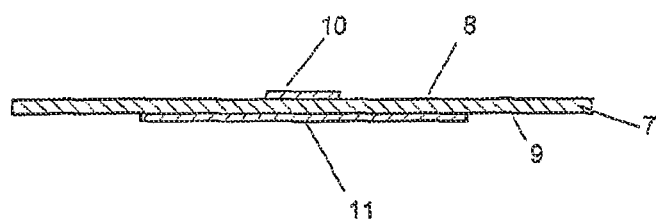
FIG. 2 shows a cross-sectional view along the line 1141 in FIG. 3a, of a piezoelectric resonator of the present invention.

The piezoelectric resonator of the present invention, shown in FIG. 2, comprises a quartz crystal plate 7 having a first crystal surface 8 and a second crystal surface 9. The first crystal surface is provided with a first electrode 10, the sensing electrode, which has a surface area of less than 15 mm², preferably less than 10 mm². The second crystal surface 9 is provided with a second electrode 11, the counter electrode. The sensing electrode 10 should preferably have a surface area of at least 0.05 mm², and should most preferably be between 1 and 5 mm². As seen in FIG. 2 the sensing electrode has a surface area that is smaller than the crystal surface area. The peripheral area surrounding the sensing electrode is intended for attachment to a flow cell element or any other clamping means for holding the crystal in a measuring cell, since the sensing electrode must not be disturbed by any clamping means during operation. The sensing electrode surface area should cover about 0.1-90% of the crystal surface area. The distance from the sensing electrode edge to the crystal edge should be at least 0.2 mm, preferably 1 mm and more preferably 2 mm.

The counter electrode 11 on the second crystal surface should preferably completely cover at least the sensing electrode area on the first crystal surface 8. However, the counter electrode should preferably be larger than the sensing electrode to assure that the complete sensing electrode area is active. This is also advantageous for manufacturing reasons, since it allows the electrodes to be slightly displaced in relation to each other, and hence the manufacture needs not to be very accurate.

Another parameter that affects the sensitivity of a QCM sensor arrangement has been found to be the flow characteristics of the fluid sample in the flow cell. Flow disturbances in the sample flow that occur in the sensing chamber as the sample passes by the sensing electrode may cause a reduction of the sensitivity. In a QCM sensor arrangement having a flow-through-cell, the sample is usually supplied to the sensing chamber from one side of the resonator crystal or from above. In the case the sample enters the Chamber from the side, it leaves at the opposite side of the crystal and thus flows parallelly over the electrode surface. In the case the sample enters from above, (perpendicularly or at an angle), the sample may leave the chamber parallelly to the electrode surface or upwards at an angle.

In the hitherto known flow-through-cell QCM sensors the width of the sensing chamber is very large in comparison to the width of the sample flow channels through which the sample is supplied to the sensing chamber. As the sample flow is lead through the sensing chamber it thus expands over the electrode surface and as a result undefined flow characteristics are caused. The change in flow conditions may include decreased flow velocity, increased turbulence, pressure variation and mixing. These circumstances lead to dispersion and dilution of the sample plug, which in turn leads to a less distinct frequency change. In many applications, e.g. in detection applications and kinetics measurements it is very important to have a low sample dispersion in the sensing chamber of the QCM sensor arrangement. Another drawback with a large sensing chamber is that pressure variations may occur over the electrode surface, with an increased noise level in the frequency signal as a result.

Figure 3A:
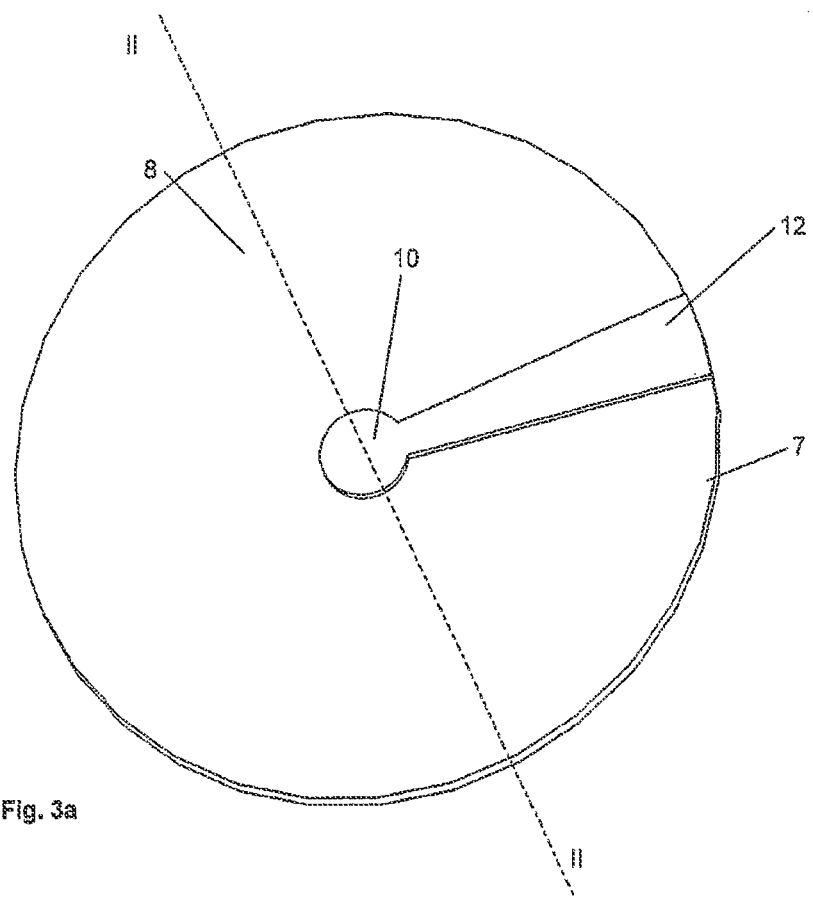
FIG. 3a shows an oblique view of a piezoelectric resonator of one embodiment of the present invention, from the sensing electrode side, i.e. the side, which is to be in contact with the sample.
Figure 3B:
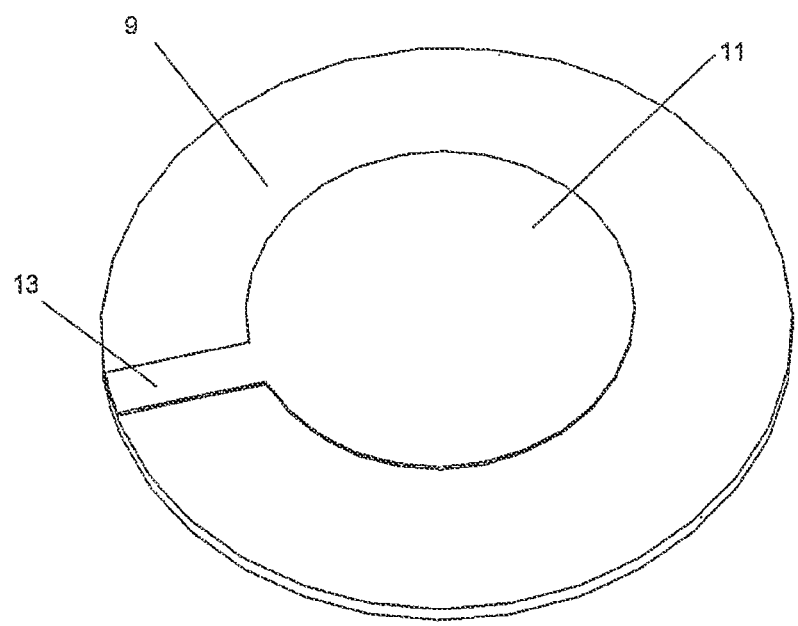
FIG. 3b shows an oblique view of the piezoelectric resonator in FIG. 3a, from the counter electrode side.

A further object of one preferred embodiment of the present invention is therefore to find a resonator which, when used in a flow cell provides improved flow characteristics. This preferred embodiment involves a resonator that has an electrode, the geometry, which is adjusted so as to fit to the flow channels of the QCM sensor arrangement. The electrode is then shaped such that the edge of the electrode facing the sample inlet is equal or slightly smaller than the width of the sample inlet. This is advantageous for electrodes of all sizes. In the case of a circular electrode (as shown in FIGS. 3a and 3b), the diameter should be slightly smaller than the diameter of the sample inlet. A resonator having a dimension that allows the flow cell to have a cross sectional area similar to that of the inlet and outlet, greatly improves the flow characteristics of the sensor arrangement. In turn, this will reduce the dispersion and increase the sensitivity of the sensor arrangement.

FIGS. 3a and 3b show oblique views of the piezoelectric resonator shown in FIG. 2. In FIG. 3a the resonator is seen from the sensing side, i.e. the side that is intended to be in contact with the sample. In FIG. 3b the resonator is seen from the counter electrode side. The crystal plate 7 of the resonator is provided with a small circular electrode 10, i.e. sensing electrode on its first side 8. The resonator is provided with a counter electrode 11 on the second side 9 as shown in FIG. 3b. Both electrodes 10, 11 preferably have contacting areas 12, 13 for connection with electrical contacts in the QCM sensor arrangement.

Figure 4:
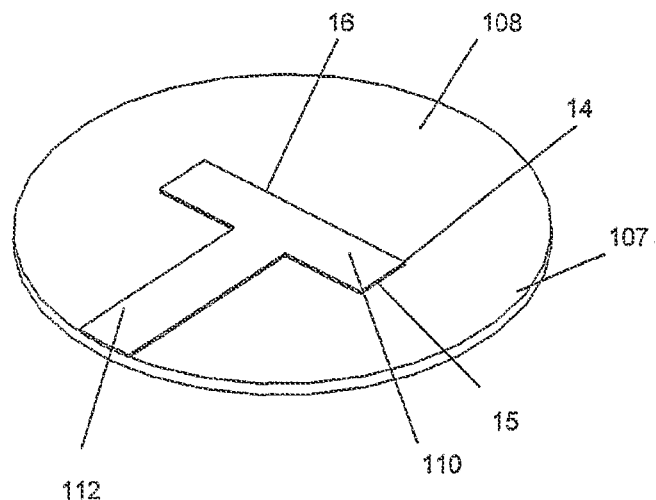
FIG. 4 shows an oblique view of a piezoelectric resonator of another embodiment of the present invention, from the sensing electrode side.

An even more preferred geometry of the sensing electrode surface is, however a rectangle or a square. FIG. 4 shows a resonator, which includes a crystal plate 107 that is provided with a rectangular electrode 110 on its first side 108 (sensing side). When a resonator as the one shown in FIG. 4. is mounted in a flow cell, the electrode 110 will have a straight edge 14 directed towards the sample inlet of a flow cell and the incoming sample plug. The flow pattern of the sample plug of a sample that is injected into and transported by the base flow unavoidably gain a parabolic shape, since the flow velocity close to the walls of a flow channel is always lower than the velocity in the middle of the channel. A straight electrode edge 14, which is perpendicular to the flow direction will result in a more immediate sensor response, resulting in a yet more distinct frequency change, since the whole width of the electrode immediately and simultaneously comes into contact with the sample plug. In addition, all parallel flow fractions of the sample will interact with the sensor electrode for an equal period of time, since each parallel flow fraction will pass the same electrode length on its way through the sensing chamber. When a rectangular shape is used for the electrode (as in FIG. 4), the rectangle is defined as having a first side 15 and a second side 16 perpendicular to said first side. The rectangle naturally has two pairs of parallel sides. For the simplicity of this description only one side of each pair is discussed, i.e. only the first side 15 and the second side 16, which belong to different pairs of sides. These first and second sides may be any one of the sides in such a pair. When the resonator is mounted in a flow cell the first side 15 will be directed towards the sample inlet, perpendicularly to the flow direction, and the second side 16 will extend parallelly to the flow direction of the sample. The proportion between the first side 15 and the second side 16 is preferably that the length of one of the sides is 0.1-10 times the length of the other side. The first side may thus be shorter than the second side (as in the example shown in FIG. 4) so that the sample passes the electrode lengthwise, but the first side 15 may alternatively be longer than the second side 16, whereby the sample passes the electrode crosswise. In the example shown in FIG. 4, the second side is 4.3 times the first side. A rectangular or square electrode is advantageous for all electrodes regardless of their size.

As shown in FIGS. 3a, 3b and 4, the first crystal surface 8, 108 is provided with a first contacting area 12, 112 connected to the first electrode 10, 110, (sensing electrode), and the second crystal surface 9 is provided with a second contacting area 13 connected to the second electrode 11 (counter electrode). The contacting areas can easily be connected to electrical contacts in the QCM sensor arrangement, whereby changes in the oscillating frequency, and thus the mass changes on the sensing electrode, can be registered. In the embodiment shown in FIG. 4 the first contacting area 12, 112 is connected to the second side 16 of the first electrode 110, i.e. to one of the sides that are parallel to the flow direction of the sample flow. Thereby the contacting area will not disturb the sample flow in the flow cell, since it will be situated outside the sensing chamber.

In some embodiments (as in the ones in FIGS. 2, 3a, 3b and 4) the quartz crystal 7, 107 used for the resonator has flat surfaces. Flat crystals are, due to their simple shape, easier to manufacture than other crystals and are therefore cheaper.

Figure 5:
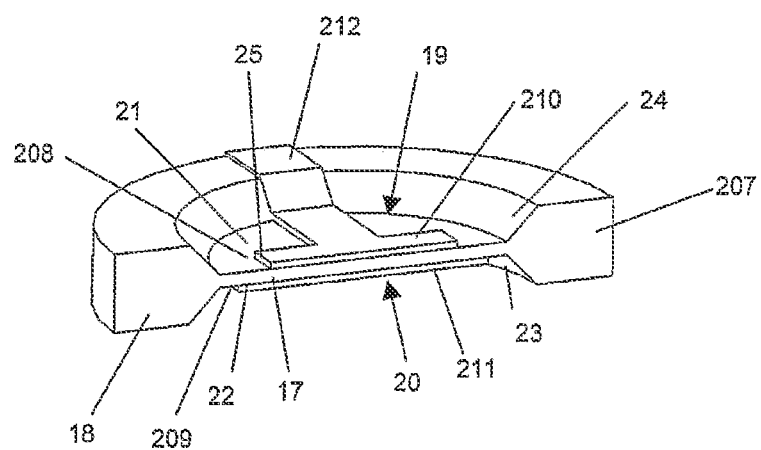
FIG. 5 shows an oblique cross-sectional view of a piezoelectric resonator of yet another embodiment of the present invention.

In another embodiment (shown in FIG. 5), the quartz crystal 207 that is used for the resonator is an inverted mesa, i.e. the crystal has a thin central region 17, which is encircled by a thicker peripheral region 18. An inverted mesa can thus withstand the fixation in a flow cell very well, and has at the same time excellent oscillating characteristics due to the low material thickness in the thin central region. The electrodes 210, 211 are situated in the thin central region 17. The inverted mesa may have recesses on both sides or on one side. The recesses have a flat bottom and the walls are sloping or straight. The thin central region 17 of the inverted mesa is thus constituted of the flat bottom of the recess/recesses. FIG. 5 shows an inverted mesa having recesses 19, 20 on both sides. A first electrode 210 is provided in the first recess 19 on the first crystal surface 208 and the second electrode 211 is provided in the second recess 20 on the second crystal surface 209. Both recesses have a flat bottom surface 21, 22 and sloping walls 23, 24. The inverted mesa structure is used to obtain a thinner crystal with higher resonance frequency and consequently higher sensitivity. The mechanical stability of the crystal is also guaranteed by the inverted mesa structure, since the peripheral region 18 of the crystal has a higher mechanical strength than the thin central region 17.

The surface area of the flat bottom 21 of the first recess 19, in which the sensing electrode 210 (first electrode) is provided, is larger than the surface area of the electrode 210. The electrode 210 is arranged in the recess 19 such that the part of the bottom surface that is not covered by the electrode surrounds the electrode. There will thus be a distance from the electrode edge 25 to the wall 23 of the recess all around the electrode.

The shortest distance from the electrode edge to the recess walls should be at least 0.01 mm. This distance ensures that dampening of the crystal oscillation is avoided.

Figure 6:
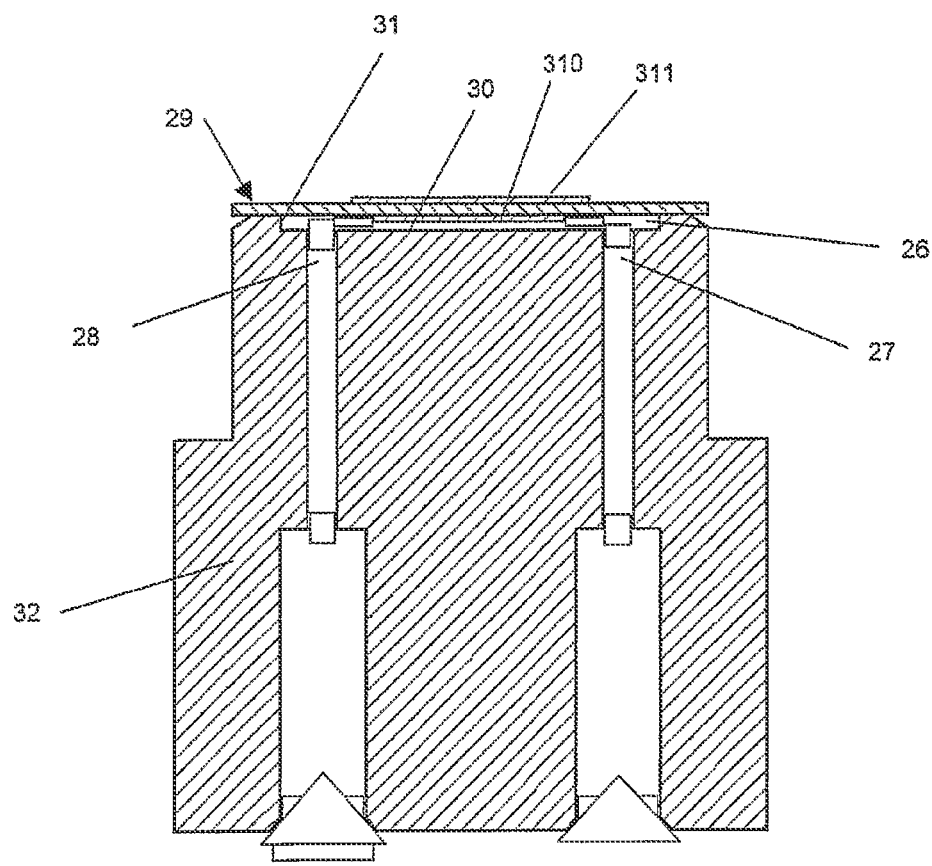
FIG. 6 shows a cross-sectional view of a flow cell in which a piezoelectric resonator of the present invention is arranged.

The present invention also relates to a flow cell for use in an arrangement for detecting or measuring an analyte in a medium. FIG. 6 shows a cross sectional view of such a flow cell. The flow cell comprises walls, which form a sensing chamber 26, inlet and outlet openings 27, 28 for leading a fluid through the sensing chamber and past a resonator 29 of any embodiment as described above. The resonator 29 is arranged in the flow cell such that it constitutes one of the walls of the sensing chamber 26 and is positioned such that the first (sensing) electrode 310 is situated inside the chamber. The resonator may be engaged in the flow cell by any suitable means, such as clamping screws, pressing or adhesive. The flow cell may be an integrated constructional part of a sensor arrangement or may be a separate detachable part that can be inserted into a sensor arrangement.

The cross sectional area of the sensing chamber perpendicular to the flow direction is less than 2.5 times the cross sectional area of the inlet and outlet openings 27, 28, whereby the flow characteristics in the flow cell are improved. Most preferably the cross sectional area is the same as the cross sectional area of the inlet and outlet openings, such that the sample flow is not affected at all by the passage through the sensing chamber. The characteristic flow channel dimension, i.e. the diameter, in the case of a circular pipe, of the inlet and outlet is preferably 0.75 mm or less. This results in a low dispersion of the sample, which in turn leads to more distinct frequency changes.

Figure 7:
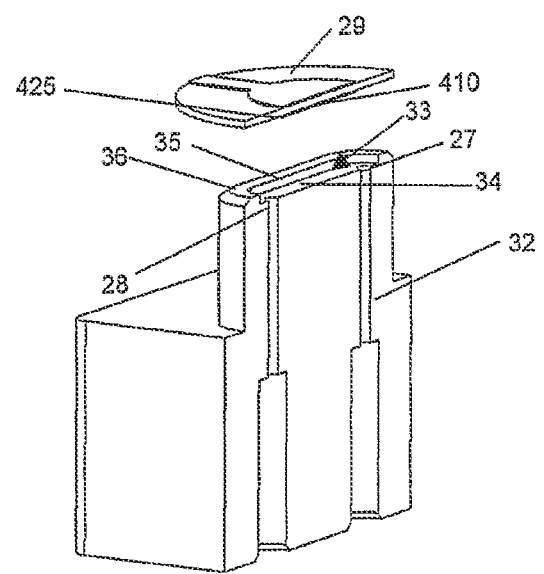
FIG. 7 shows an oblique cross-sectional exploded view of a flow cell in which comprises a piezoelectric resonator of the present invention and a flow cell element.

The walls 30, 31 of the flow cell that are not constituted of the resonator 29 may be assembled of different parts. However, in a preferred embodiment (shown in FIG. 7) the flow cell comprises a flow cell element 32 that includes an outwardly open recess 33. The recess has a bottom surface 34 and walls 35, whereby said bottom and walls constitute the walls of the sensing chamber that are not provided by the resonator 29. In this embodiment the resonator is a replaceable part, which is held against the flow cell element by a pressing force so as to cover the recess and thus forming one wall of the flow cell. As an alternative the resonator may be attached to the flow cell element by an adhesive. In that case the whole flow cell is a replaceable part. The flow cell element comprises a contact surface 36, against which the resonator is to be held. The contact surface 36 is plane-parallel to the bottom 34 of the recess 33 and encircles the recess. In order to improve the flow characteristics the recess has a geometrical shape that corresponds to the geometry of the sensing electrode 410. The shortest distance from the electrode edge 425 to the recess walls 35 is preferably at least 0.01 mm, thereby assuring the free oscillation of the electrode 410. IF the resonator is an inverted mesa the resonator 29 may preferably be arranged in the flow cell such that the flat contact surface 36 abuts against the thick peripheral region 18 of the resonator. In some applications it may be suitable to let the contact surface 36 abut against the bottom 21 of the resonator.

A flow cell element for use together with an inverted mesa resonator may alternatively have the same shape as the flow cell element 32, as described above, but without the recess. The flow cell element will thus have a flat surface that is intended for abutment against the thick peripheral region 18 of the resonator and has inlet end outlet openings for the sample. The flat flow cell element surface, the flat bottom 21 and the walls 24 of the resonator will then constitute the sensing chamber 26.

The present invention also relates to a sensor arrangement for detecting or measuring an analyte in a medium, which comprises a flow cell as the one described above. The flow cell used thus includes a resonator of the present invention.

The resonator of the present invention can be used in QCM sensor arrangement for analysis of the viscosity of a liquid sample and are particularly suitable for studying chemical and biochemical interactions. If a piezoelectric sensor is to be used for the latter purpose, the electrode that is to be exposed to the sample is provided with a specific surface coating, which will interact with the sample. Such surface coated piezoelectric sensors can be used within for example surface science, biotechnology research and pharmaceuticals development. Other applications can be as sensor for detection of hazardous gases or substances such as environmental contaminants, biochemical warfare agents and illicit drugs, e.g. narcotic substances or performance improving drugs (doping). A third area for application of the technology is health diagnostics, where the sensor can be used for examining patients for different diseases by analysis of human blood or other body fluids.

Example

To a piezoelectric circular quartz crystal (10 MHz AT-cut) with a small rectangular sensing electrode of 1 mm×4 mm a droplet (20 µl) of Bovine Serum Albumin (BSA) solution of 1 mg/ml in Phosphate buffered saline (PBS) was applied and allowed to dry at room temperature. Subsequently, the crystal was inserted into an Attana 100 QCM system, provided by Attana AB, Stockholm, Sweden, with a flow chamber of rectangular geometry (5 mm×1.5 mm) corresponding to the shape of the electrode. The electrode and the flow chamber were oriented such that the short side of the electrode was perpendicular to the flow direction.

The first electrode was exposed to a continuous flow of PBS solution at a flow rate of 100 µl minute. A sample plug of 50 µl of de-ionised water was inserted into the flow by means of a Vici chromatography 8-way injection valve, provided by Scantec lab, Partilie, Sweden. The frequency shift was monitored after the insertion of the water sample and the data is presented in FIG. 8 and FIG. 9 with the dashed line.

Next, a standard circular crystal (10 MHz AT-cut) with a circular gold sensor electrode of 4.5 mm diameter was treated similarly with a droplet (20 µl) of BSA solution of 1 mg/ml PBS. The crystal was then inserted into an Attana 100 QCM system with a flow chamber of circular geometry (5 mm diameter) corresponding to the shape of the first electrode. The electrode was exposed to a continuous flow of PBS solution at a flow rate of 100 µl minute and a sample plug of 50 µl of de-ionised water as described above. The frequency shift was monitored after the insertion of the water sample and the data is displayed in FIG. 8 and FIG. 9 with a solid line.

Two distinct differences in behaviour can be observed: (1) A huge difference in sensitivity of the sensor and (2), a difference in shape of the frequency response curve due to the difference in fluidics and dispersive phenomena of the two designs.

Figure 8:
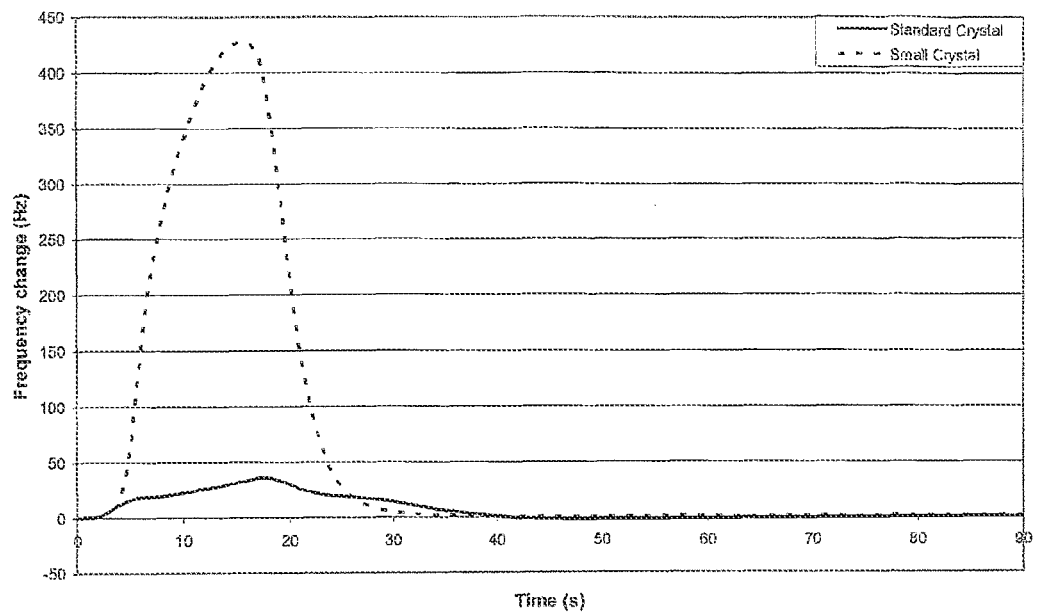
FIG. 8 shows comparison graphs for an improved electrode and a standard electrode.

The graphs of FIG. 8 show that the frequency response of the standard electrode peaks at 36 Hz, whereas the small electrode peaks at 430 Hz. The sensitivity in measuring the difference between PBS solution and de-ionised water of the small (4 $mm^2$) electrode was thus much higher than the sensitivity of the standard (15.9 $mm^2$) electrode, a sensitivity increase exceeding a factor of ten.

Figure 9:
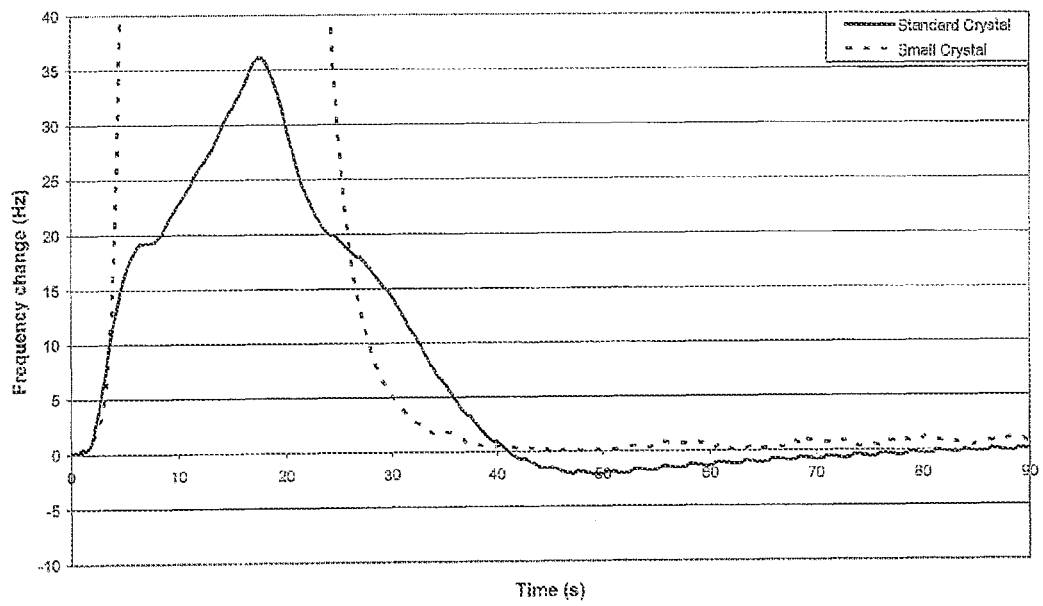
FIG. 9 shows an enlargement of the lower part of the graphs of FIG. 8.

FIGS. 8 and 9 also indicate a difference in peak shape between the rectangular electrode peak in and the circular electrode peak. This is mainly a result of the different electrode geometries.

In an ideal sensor system with a plug flow through the channels and the sensor chamber the shape of the response should be completely square starting with a step rise in the frequency at time zero and ending with a step decrease after 30 s. Such ideal systems do not exist, since the flow in a laminar system will take a parabolic shape, which together with radial and axial diffusion inevitably leads to mixing in the interface between the sample plug and the continuous running buffer. The mixing will occur primarily at the beginning and the end of the sample plug leading to diluted sample concentrations in those regions. The phenomenon is often referred to as dispersion.

A comparison of the two graphs for the rectangular and the circular electrodes shows that a system using a rectangular electrode is much closer to the ideal system than the circular one. Detailed analyses of the graphs show that the difference by the introduction of the sample to the sensing surface is rather negligible. The difference in behaviour when the sample plug leaves the chamber is, however, quite significant. By the time that the ideal plug should have left the chamber, 30 s, the rectangular system show a signal of approximately 1% of its maximum frequency shift. The response of the circular system remains at 39% of its maximum frequency shift at the same time, thereby having a quite substantial lag, which may considerably impair the quality of measurements.

Other phenomena that may occur in these analysis systems are local turbulence and irregular flow patterns. Irregular flow patterns can be created in regions where the flow is exposed to rapid changes in the characteristic flow dimensions (e.g. cross sectional area), which will for instance occur when the flow enters the circular flow chamber. The change in cross sectional area will cause a local pressure drop in sensor chamber, possibly resulting in local micro eddies and general irregularities in the flow, which in turn will increase the deviation from the idealised conditions described above. The irregular shape of the response from the circular system suggests that phenomena of this type occur in the circular system. The change in cross sectional area is significantly less for the sensor system with the rectangular electrode and, consequently, the response from that system contains no unexpected irregularities.

The invention claimed is:

1. A flow cell for use in an apparatus for detecting or measuring an analyte in a liquid medium, comprising:
   a flow cell element having an outwardly open recess, including a bottom surface and walls of a sensing chamber,
   a resonator that constitutes a further wall enclosing the sensing chamber and arranged such that a first electrode is situated inside the sensing chamber, and
   inlet an outlet openings having a diameter of 0.75 mm or less, for leading the liquid medium through the sensing chamber,
   wherein the resonator is a thickness shear mode piezoelectric resonator comprising a quartz crystal plate having a first crystal surface and a second crystal surface, the first crystal surface being provided with the first electrode having an edge and the second crystal surface being provided with a second electrode, and
   wherein the resonator is attached to the flow cell element at the peripheral area surrounding the first electrode so as to cover the recess and form the flow cell, the first electrode of the resonator has a surface area of at least 0.05 $mm^2$ and less than 15 $mm^2$, and the shortest distance from the electrode edge to the walls of the sensing chamber is at least 0.01 mm.

2. The flow cell of claim 1, wherein the surface area of the first electrode is less than 10 $mm^2$.

3. The flow cell of claim 1, wherein the surface area of the first electrode is between 1-5 $mm^2$.

4. The flow cell of claim 1, wherein the surface area of the first electrode is smaller than the first crystal surface area.

5. The flow cell of claim 1, wherein the distance from the first electrode edge to the crystal edge is at least 0.2 mm.

6. The flow cell of claim 1, wherein the first electrode is a sensing electrode.

7. The flow cell of claim 1, wherein the first and second surfaces of the quartz crystal are flat.

8. The flow cell of claim 1, wherein the sensing chamber has a volume of less than 2 μl.

9. The flow cell of claim 1, wherein the resonator is a replaceable part, which is held against the flow cell element so as to cover the recess and thus form the flow cell.

10. The flow cell of claim 1, wherein the first electrode has a surface that has the shape of a rectangle, having a first side and a second side.

11. The flow cell of claim 10, wherein the first side is at least 0.01-10 times the second side.

12. The flow cell of claim 1, wherein the first crystal surface is provided with a first contacting area connected to the first electrode, and the second crystal surface is provided with a second contacting area connected to the second electrode.

13. The flow cell of claim 12, wherein the first contacting area is connected to the second side of the first electrode.

14. The flow cell of claim 1, wherein the quartz crystal is an inverted mesa, having a thin central region in which the first electrode is provided.

15. The flow cell of claim 14, wherein the first side of the crystal has at least a first recess in which the first electrode is provided, said first recess having a wall and a bottom surface, the area of the bottom surface being larger than the first electrode, and wherein the first electrode is arranged in the recess such that there is a distance between the electrode edges and the recess walls.

16. The flow cell of claim 1, wherein the cross sectional area of the sensing chamber perpendicular to the flow direction is less than 2.5 times the cross sectional area of the inlet and outlet openings.

17. The flow cell of claim 16, wherein the cross sectional area of the sensing chamber perpendicular to the flow direction is the same as the cross sectional area of the inlet and outlet openings.

18. The flow cell of claim 1, wherein the resonator is attached to the flow cell element by an adhesive so as to cover the recess and thus form the flow cell.

19. The flow cell of claim 18, wherein the flow cell element comprises a contact surface, against which the resonator is to be held, which is plane-parallel to the bottom of the recess and which encircles the recess, and wherein the recess has a geometrical shape that corresponds to the geometry of the first electrode.

* * * * *